United States Patent [19]

Long et al.

[11] Patent Number: 4,560,646
[45] Date of Patent: Dec. 24, 1985

[54] PROTECTED DEVELOPING AGENTS

[75] Inventors: William E. Long, Wilmslow; Norman A. Smith, Holmes Chapel; Terence C. Webb, Wilmslow; Stephen R. Postle, Wilmslow; Kenneth M. McCombe, Altringham; Martin C. Grossel, Surbiton, all of England

[73] Assignee: Ciba Geigy AG, Basle, Switzerland

[21] Appl. No.: 673,625

[22] Filed: Nov. 21, 1984

[30] Foreign Application Priority Data

Nov. 23, 1983 [GB] United Kingdom ................ 8331264

[51] Int. Cl.$^4$ .......................... G03C 1/02; G03C 5/30
[52] U.S. Cl. .................................... 430/566; 430/443; 430/959
[58] Field of Search ............... 430/556, 552, 553, 443, 430/566, 959

[56] References Cited

U.S. PATENT DOCUMENTS 2,269,481 1/1942 Reindorp ............................ 430/556
4,446,216 5/1984 Smith et al. ......................... 430/959

Primary Examiner—Mary F. Downey
Attorney, Agent, or Firm—Joseph G. Kolodny

[57] ABSTRACT

Compounds of the formula

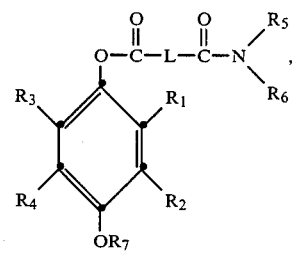

wherein L is a direct bond or consists of a chain of carbon atoms or of a divalent ring system, $R_1$ to $R_4$ are hydrogen or alkyl, $R_5$ or $R_6$ are hydrogen, alkyl or aryl, or $R_5$ together with $R_6$ complete a ring system, and $R_7$ is hydrogen or a group of the formula

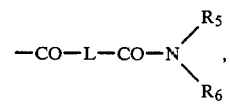

wherein L, $R_5$ and $R_6$ are as defined.

These compounds are useful developing agents for activation processing.

2 Claims, No Drawings

PROTECTED DEVELOPING AGENTS

This invention relates to protected developing agents to their use in photographic material.

Hydroquinone is the most widely used developing agent for developing latent silver images in silver halide photographic material. Most usually exposed photographic material is processed in a bath containing hydroquinone to develop the latent image but for some types of processing it is preferable that the hydroquinone is present already in the photographic material which after exposure is processed in an alkali bath to develop the latent image as hydroquinone only acts as a developing agent under alkaline conditions. Such a method of processing is known as activation processing. Activation processing is extremely rapid but it is not widely employed except in certain special circumstances where the disadvantages of incorporating hydroquinone into the photographic material outweigh the advantages. These disadvantages include developer decomposition on ageing and interference with the setting and hardening of the gelatin or other colloidal layers in which it is incorporated during the coating of the photographic material. Further, activation processing often tends to cause stain and tanning of the processed material.

In an effort to overcome these disadvantages it has been proposed to use protected hydroquinones which are substituted hydroquinones in which the protecting group or groups are cleaved at the high pH-value of the alkaline processing bath. However it has proved difficult to find substituted hydroquinones which are readily cleavable in the alkaline bath and thus which release the active hydroquinone quickly enough to achieve rapid processing and also substituted hydroquinones which are stable during coating and on storage of the photographic material. Many of the proposed substituted hydroquinone compounds contain in the protective moiety desensitising groups which limit the use of such compounds, or are coloured due to the presence of chromophoric groups, such as nitro groups, in the protective moiety. Such coloured compounds may be of use in certain circumstances but their presence tends to cause speed losses in the photographic material.

Some of the proposed hydroquinone derivatives are water-insoluble and these compounds comprise comparatively bulky water-insolubilising groups which lead to high coating weights. The presence of high molecular weight components in a layer of a photographic material often leads to poor inter-layer or layer/base adhesion and poor layer hardening. Examples of water-insoluble hydroquinone derivatives are given in Research Disclosure 16444 of December 1977.

We have found a class of substituted hydroquinone compounds which are water-insoluble, cleave rapidly in alkaline solution and exhibit superior storage stability and little tendency to cause stain or tanning problems when material which contains them is activation processed. Furthermore, none of the compounds are coloured nor do they contain any desensitising groups, and all can be formulated easily in photographic layers.

It is thus one object of the present invention to provide substituted hydroquinone compounds of formula

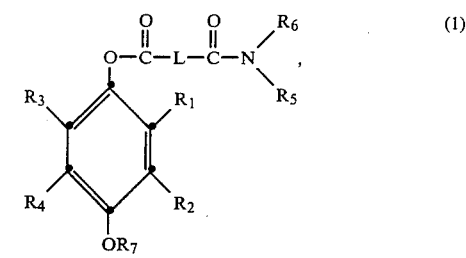

wherein the linking group L is a direct bond or consists of a chain of carbon atoms, which may be saturated or unsaturated, or consists of a divalent ring system or divalent ring systems, where all of which may be substituted, $R_1$, $R_2$, $R_3$ and $R_4$ are each hydrogen, halogen or optionally substituted alkyl, $R_5$ and $R_6$ are each hydrogen or optionally substituted alkyl or aryl or $R_5$ together with $R_6$ represent the atoms necessary to complete an optionally substituted ring system or optionally substituted ring systems, and $R_7$ is hydrogen or a group of formula

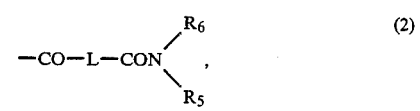

wherein L, $R_5$ and $R_6$ are as defined above.

A further object of the present invention is a process for the preparation of the inventive hydroquinone compounds. Another object is a photographic material containing these hydroquinone compounds. Still another object is the use of this photographic material for the production of photographic images.

In the hydroquinone compounds of the formula (1), the linking group L is a dirct bond or consists of a chain of carbon atoms, which may be saturated or unsaturated. Alkylene chains containing 1 to 4 carbon atoms such as methylene, ethylene, propylene or butylene and alkenylene chains containing 1 to 4 carbon atoms such ethenylene, propenylene, 1- or 2-butenylene or 1,4-butadienylene constitute the preferred chain systems. Another group of suitable linking groups L is represented by divalent ring systems such as cyclohexylene, cyclopentylene, phenylene and naphthylene. Said chains of carbon atoms as well as said divalent ring systems are optionally substituted. As suitable substituents there may be mentioned alkyl and alkoxy radicals, preferably each containing 1 to 4 carbon atoms, aryl or aryloxy such phenyl and phenoxy; further halogen, preferably fluorine, chlorine or bromine, amino, substituted, preferably alkyl substituted amino, and also carboxylic acid, ester or amide groups, preferably each containing 1 to 6 carbon atoms.

The substituents $R_1$ to $R_4$ denote independently from each other hydrogen, alkyl, preferably containing 1 to 4 carbon atoms such as methyl, ethyl, propyl, i-propyl, or t-butyl, or halogen, for example fluorine, chlorine or bromine. These alkyl radicals may be substituted by those substituents mentioned above for the carbon atom chains and divalent ring systems L.

Substituent $R_7$ represents either hydrogen or the group of the formula

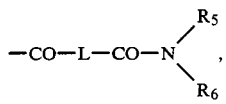 (2)

wherein L is as defined above and $R_5$ and $R_6$ independently from each other are hydrogen, alkyl having 1 to 4 carbon atoms such as methyl, ethyl, propyl or butyl, or $R_5$ and $R_6$ together with the nitrogen atom to which they are bonded form a saturated or unsaturated 6-membered ring, which optionally contains nitrogen and/or oxygen atoms, such as cyclohexyl, methylcyclohexyl, piperazinyl, N-methylpiperazinyl, morpholinyl, phenyl or tolyl.

In preferred compounds of the formula (1), L is a direct bond, alkylene or alkenylene each having 1 to 4 carbon atoms or phenylene.

More preferred are those compounds, wherein L is a direct bond, methylene, ethylene, ethenylene or 1,2-phenylene.

Most preferably, L is a direct bond.

$R_1$ to $R_4$ in suitable compounds of the formula (1) are independently from each other hydrogen or alkyl, preferably having 1 to 4 carbon atoms, or, more preferably, $R_1$ to $R_4$ are all hydrogen.

Substituent $R_7$ is preferably hydrogen.

Preferably, $R_5$ and $R_6$ independently from each other are hydrogen, alkyl having 1 to 4 carbon atoms or $R_5$ and $R_6$ form together with the nitrogen atom to which they are bonded a saturated or unsaturated 6-membered ring, optionally containing further hetero atoms such as nitrogen and/or oxygen.

More preferably, $R_5$ and $R_6$ independently from each other are hydrogen, methyl, ethyl, butyl, or $R_5$ and $R_6$ form together with the nitrogen atom to which they are bonded a N-methylpiperazinyl, morpholinyl or p-tolyl radical.

Those compounds of the formula (1), wherein $R_5$ and $R_6$ are alkyl having together a total of 2 to 8 carbon atoms, are particularly suitable.

Compounds of formula (1) may be prepared by reacting a hydroquinone compound of formula

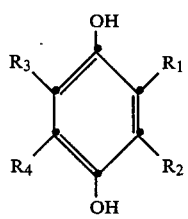 (3)

in which $R_1$, $R_2$, $R_3$ and $R_4$ are as defined above, with an acid chloride of formula:

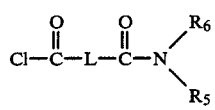 (4)

in which L, $R_5$, $R_6$ are as defined above, in the presence of a base.

Acid chlorides of formula (3) may be prepared by known routes, for example, reaction of thionyl chloride with an acid of formula

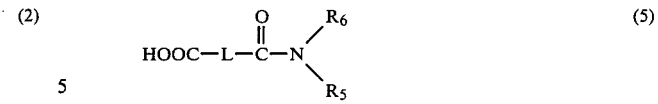 (5)

in which L, $R_5$ and $R_6$ are as defined above, or, preferably, by the controlled reaction of a diacid chloride of formula

 (6)

in which L is as defined above, with an amine salt of formula

 (7)

in which $R_5$ and $R_6$ are as defined above and $X^\ominus$ is an anion, for example chloride.

According to another aspect of the present invention there is provided photographic silver halide material which comprises on a support at least one colloid silver halide layer there being present either in the silver halide layer or in a layer in operative contact therewith a substituted hydroquinone of formula (1).

By layer in operative contact therewith is meant either an adjacent layer or a layer so close to the silver halide layer that the hydroquinone generated in that layer can diffuse to the silver halide layer.

Usually silver halide photographic material which is to be activation processed comprises only one colloid silver halide layer and most usually this colloid is gelatin.

Therefore, according to a preferred embodiment of this aspect of the present invention there is provided photographic silver halide material which comprises coated on a support a gelatine silver halide emulsion layer which comprises a substituted hydroquinone of formula (1).

The amount of the compound of formula (1) present in the silver halide photographic material will depend on the actual compound used and on the proposed use of the photographic material. Preferably, however, the compound of formula (1) is present in the photographic material in an amount within the range of 0.1 to 1.0 moles per 1.5 moles of silver halide present in the photographic material.

Preferably, the substituted hydroquinones of formula (1) are dispersed in the layer of the photographic material as a solid dispersion which has been obtained by ball-milling the solid in an aqueous medium in the presence of a wetting agent. Alternatively, the water-insoluble compounds of formula (1) may be dispersed in the layer of the photographic material in an oil (high boiling organic solvent) for example tricresyl phosphate.

The silver halide present in the photographic material may be any one of the normally employed silver halides such as silver chloride, silver bromide, silver chlorobromide, silver bromoiodide and silver iodochlorobromide.

The silver halide emulsions may be optically sensitised by the presence therein of optical sensitising dyes, for example merocyanine or carbocyanine dyes.

The silver halide emulsions may contain any of the additives commonly used in photographic emulsions, for example stabiliser agents such as tetra-azaindenes, metal sequestering agents and growth or crystal habit modifying agents commonly used for silver halide, such as adenine.

Preferably, the colloid medium is gelatin or a mixture of gelatin and a water-soluble latex, for example a latex of a vinyl acrylate-containing polymer. Most preferably, if such a latex is present in the final emulsion, it is added after all crystal growth has occurred. However, other water-soluble colloids, for example casein, polyvinyl, pyrrolidone or polyvinyl alcohol, may be used alone or together with gelatin.

The support may be any one of the supports normally used for photographic materials including paper base, polyethylene terephthalate, cellulose triacetate, cellulose acetate buytyrate, polystyrene and polycarbonate.

The photographic material of the present invention may be used in a large number of different ways including black and white print material, X-ray film material, colour film material, microfilm products and direct positive material.

The photographic material of the present invention most usually is prepared by forming an aqueous colloid coating solution of the silver halide which comprises a dispersion of the compound of formula (1) and this colloid coating solution is coated as a layer on a support and dried.

After exposure the photographic material may be treated with an activator solution, which is an aqueous alkaline solution which comprises for example sodium hydroxide or sodium carbonate. Most usually the activator solution will have a pH-value of between 10 and 14. Stabilisers, antifoggants and development accelerators may also be present in the activator solutions.

The activator solutions may be applied to the exposed photographic material of the present invention in all the usual ways such as surface application, total immersion of the material in the activator solution and spraying.

After the photographic material of the present invention has been activator processed it may be fixed in a silver halide fixing solution, for example ammonium thiosulphate, to remove the undeveloped silver halide, or it may be stabilised to render the remaining silver halide light-insensitive by treatment with a known stabiliser treatment solution, for example an aqueous ammonium thiocyanate solution.

Representative compounds of the present invention are the compounds of the following formulae:

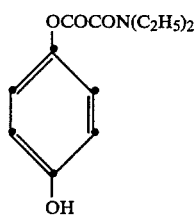
(8)

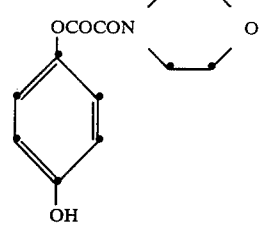
(9)

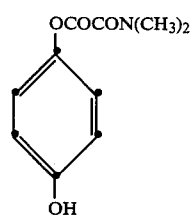
(10)

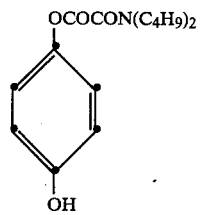
(11)

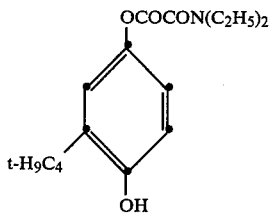
(12)

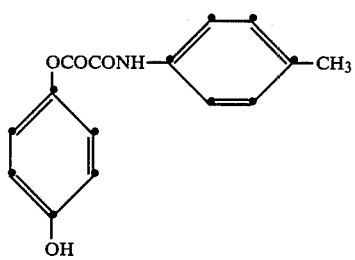
(13)

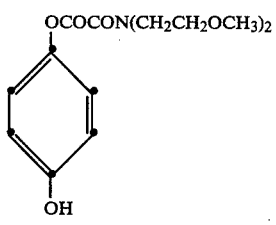
(14)

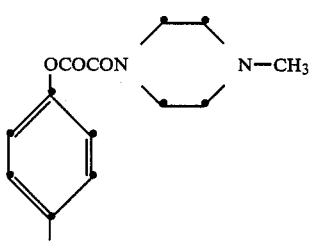
(15)

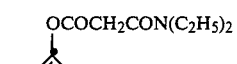(16)

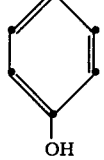

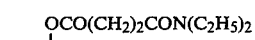(17)

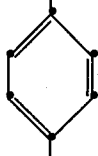

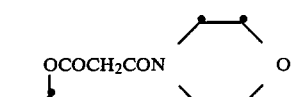(18)

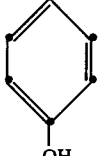

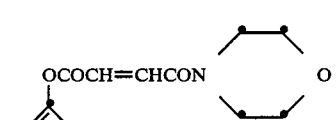(19)

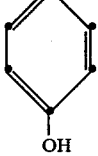

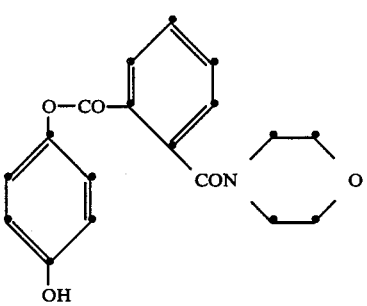(20)

(21)

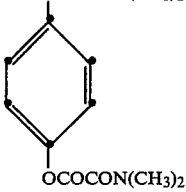

The following Examples will serve to illustrate the invention.

EXAMPLE 1

Preparation of the compound of formula (8)

Diethyloxamyl chloride (10 g, prepared according to Chem. Abs. 56:4744f) in acetone (20 ml) was added dropwise to a cooled, stirred solution of hydroquinone (18 g) in pyridine (7 ml) and acetone (250 ml) over 20 minutes. The mixture was stirred for 3 hours and then poured into water (500 ml). The aqueous mixture was then extracted with ethylacetate (600 ml) and the solvent removed to yield a solid, which was washed with water and recrystallised from an ethyl acetate/hexane mixture yielding the compound of formula (8) in crystalline form (7 g), melting point 125° to 127° C.

The compounds of the formula (9), (10), (11) and (12) having melting points of 139° to 142°, 147° to 148°, 55° to 58° and 143° to 147° C., respectively, were prepared similarly.

The compound of the formula (21), melting point 155° to 157° C., was prepared analogously using 2 moles of the appropriate acid chloride to 1 mole of hydroquinone.

EXAMPLE 2

Preparation of the compound of formula (13)

The intermediate acid chloride of the formula

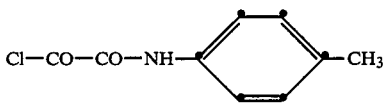(22)

was prepared by stirring p-toluidine hydrochloride (7 g) with oxalylchloride (6 ml) in dichloromethane (5 ml) for 18 hours at room temperature. Dichloromethane (30 ml) was added to the reaction mixture which was then filtered. Removal of the solvent yielded a solid which was recrystallised from cyclohexane to give the compound of the formula (22) as cream plates (9 g), melting point 96° to 98° C.

The compound of the formula (13) was prepared as follows from the acid chloride. The acid chloride of the formula (22) (5 g) was added to a solution of hydroquinone (2.8 g) in acetone (35 ml) at 10° to 15° C. Pyridine (2 ml) was then added and the mixture stirred for 1 hour. The mixture was filtered and the solvent removed to yield an oil which solidified on the addition of water (50 ml) to give the compound of the formula (13) (4 g), melting point 220° to 222° C.

EXAMPLE 3

Preparation of the compound of the formula (17)

The intermediate amide of the formula

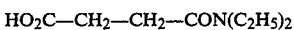(23)

was prepared by refluxing succinic anhydride (20 g) and diethylamine (30 ml) in cloroform for 1 hour. Removal of the solvent gave a residue which was poured into dilute hydrochloric acid (200 ml). The acid compound of the formula (23) was extracted with chloroform (200 ml) and dried (MgSO₄). Removal of the solvent and recrystallisation from toluene gave the compound of the formula (23) in form of a white solid (25 g), melting point 84° to 85° C.

Preparation of the compound of the formula (17)

The acid compound of the formula (22) (20 g) was refluxed with thionyl chloride (30 ml) for 1 hour. The excess thionyl chloride was removed and the residue added dropwise to a cooled stirred solution of hydroquinone (26 g) and pyridine (10 ml) in acetone (50 ml). After stirring for 2 hours, the solvent was removed and the residue added to water. The product compound of the formula (17) was extracted with ethyl acetate and washed with water to yield a crystalline solid, melting point 152° to 154° C.

EXAMPLE 4

Use Example: Preparation of a solid dispersion of the compound of the formula (8)

The following mixture was prepared:
0.2 g compound of the formula (8)
5 ml distilled water
0.25 ml anionic wetting agent (30% aqueous solution)
15 g 2 mm glass beads The above ingredients were added to a sealed plastic container and ball milling was effected using a high-speed mixer-mill for 30 minutes. The dispersion was separated from the glass beads by filtration and 10 ml aliquots of coating solution made up according to the following formula:
5 ml solid dispersion (as described above)
1.5 ml silver chlorobromide emulsion (Ag 25 mg/dm$^2$)
1 ml 1% aqueous formaldehyde solution
Water to 10 ml The solution was coated at 40° C. on triacetate film base attached to a glass plate, set at 5° C. and dried:
overall silver coating weight: 25 mg/dm$^2$
overall gell coating weight: 80 mg/dm$^2$
overall compound of the formula (8) coating weight: 82 mg/dm$^2$ The coating thus obtained was exposed in an overall manner and treated with an activator solution consisting of 2 molor sodium hydroxide (pH 14) for 20 seconds. The coating was then washed, fixed in an ammonium thiosulphate solution (100 g/l) for two minutes in a bath, washed and then dried.

The silver density obtained by this method was 2.53. Thus, this compound exhibited good reactivity and hence a good maximum density at this pH-value.

A$D_{max}$-value of 1.0 usually indicates a poor reactivity of the hydroquinone used, whereas 1.5 is considered an acceptable $D_{max}$-value, which shows the sufficient reactivity of the corresponding hydroquinone.

Solid dispersions of the compounds of the formulae (9), (10), (12), (13), (17) and (21) were prepared in a similar manner. Likewise, similar coating solutions were prepared from these dispersions and after coating each on triacetate film base each of the coatings was overall light exposed and processed in a similar manner to the coating of the compound of the formula (8). The $D_{max}$-values thus obtained were as follows:

| Compound of the formula | $D_{max}$ |
|---|---|
| (9) | 2.44 |
| (10) | 1.77 |
| (12) | 2.66 |
| (13) | 2.57 |
| (17) | 2.48 |
| (21) | 1.64 |

Thus, all these compounds also exhibited good reactivity at a pH-value of 14.

We claim:

1. Photographic silver halide material which comprises, on a support, at least one colloid silver halide layer, there being present either in the silver halide layer or in a layer in operative contact therewith, a compound of the formula

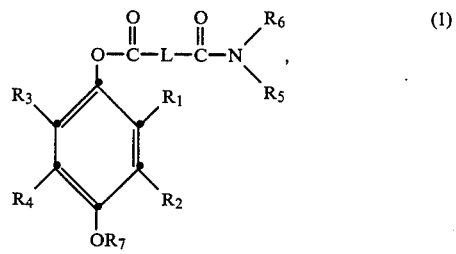

wherein the linking group L is a direct bond, alkylene or alkylene each having 1 to 4 carbon atoms or phenylene, all of which may be substituted, $R_1$, $R_2$, $R_3$ and $R_4$ are each hydrogen, unsubstituted or substituted alkyl or halogen, $R_5$ and $R_6$ are each hydrogen or methyl, ethyl, butyl p-tolyl, or combine to form a N-methylpiperazinyl or morpholinyl ring and $R_7$ is hydrogen or a group of formula

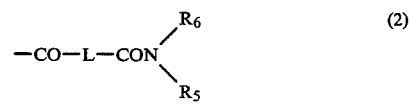

wherein L, $R_5$ and $R_6$ are as defined above.

2. Photographic silver halide material according to claim 1, wherein the compound is present in the silver halide emulsion layer.

* * * * *